United States Patent [19]
Horikoshi et al.

[11] Patent Number: 5,614,542

[45] Date of Patent: Mar. 25, 1997

[54] THIAZOLIDINE DERIVATIVES HAVING ANTI-HYPERTENSIVE ACTIVITY AND THEIR THERAPEUTIC USE

[75] Inventors: Hiroyoshi Horikoshi; Toshihiko Fujiwara; Shinji Yoshioka; Hiroshi Nishino; Hiroyuki Koike; Takao Yoshioka, all of Tokyo, Japan

[73] Assignee: Sankyo Company, Limited, Tokyo, Japan

[21] Appl. No.: 456,287

[22] Filed: May 31, 1995

Related U.S. Application Data

[63] Continuation of Ser. No. 206,027, Mar. 2, 1994, abandoned, which is a continuation of Ser. No. 24,826, Mar. 1, 1993, abandoned, which is a continuation of Ser. No. 890,283, May 26, 1992, abandoned, which is a continuation of Ser. No. 642,415, Jan. 17, 1991, abandoned.

[30] Foreign Application Priority Data

Jan. 22, 1990 [JP] Japan ..................... 2-012321

[51] Int. Cl.$^6$ ................................. A61K 31/425
[52] U.S. Cl. ......................... 514/369; 514/929
[58] Field of Search ..................... 514/369, 929

[56] References Cited

U.S. PATENT DOCUMENTS

| | | | |
|---|---|---|---|
| 4,572,912 | 2/1986 | Yoshioka et al. | 514/369 |
| 4,873,255 | 10/1989 | Yoshioka et al. | 514/369 |
| 4,933,355 | 6/1990 | Yoshioka et al. | |
| 5,053,420 | 10/1991 | Pershadsingh et al. | 514/369 |

OTHER PUBLICATIONS

Characterization of New Oral Antidiabetic Agent CS–045, Fujiwara et al, Diabetes, vol. 37, Nov. 1988, pp. 1549–1558.
Studies on Hindered Phenols and Analogues. 1. Hypolipidemic and Hypoglycemic Agents with Ability To Inhibit Lipid Peroxidation, Yoshioka et al, J. Med. Chem. 1989, 32, pp. 421–428.
CA 113(17):144852d, Faermark et al. (1990).
CA 108(5):31590u, Takada (1986).

*Primary Examiner*—Kimberly Jordan
*Attorney, Agent, or Firm*—Frishauf, Holtz, Goodman, Langer & Chick, P.C.

[57] ABSTRACT

Thiazolidine derivatives of formula (I):

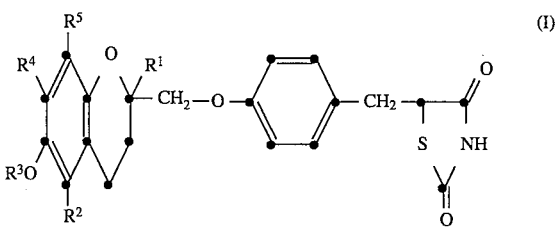

(in which: $R^1$, $R^2$, $R^4$, $R^5$ are each hydrogen or alkyl; and $R^3$ is hydrogen, aliphatic acyl, alkoxy-carbonyl, or arylcarbonyl and pharmaceutically acceptable salts thereof are anti-hypertensive agents and are useful in the treatment of obesity-related hypertension.

2 Claims, No Drawings

THIAZOLIDINE DERIVATIVES HAVING ANTI-HYPERTENSIVE ACTIVITY AND THEIR THERAPEUTIC USE

This application is a Continuation, of application Ser. No. 08/206,027, filed Mar. 2, 1994, now abandoned, which is a continuation of application of Ser. No. 08/024,826, filed Mar. 1, 1993 (abandoned), which is a continuation of application Ser. No. 07/890,283, filed May 26, 1992 (abandoned), which is a continuation of application Ser. No. 07/642,415, filed Jan. 17, 1991 (abandoned).

BACKGROUND TO THE INVENTION

The present invention relates to a series of thiazolidine derivatives which have anti-hypertensive activity, and which have been found to be especially useful in the treatment and prophylaxis of hypertension associated with obesity.

Hypertension (or elevated blood pressure) is a condition that can threaten life or can reduce the quality of life of sufferers. It is well established that a reduction in blood pressure can significantly reduce the risks of morbidity and mortality. Obesity has been shown conclusively to be a significant contributing factor in the development of hypertension, and hypertension has been observed much more frequently in obese individuals than in those of normal body weight. Hypertension of this type has also been shown to be a risk factor which may induce the development of coronary artery disease [Kennel, et el. Intern. Med. 67 48–59 (1967); Stamler et al. J. Amer. Med. Assoc. 240 1607–1610 (1978)]. Obesity-related hypertension is classified as essential hypertension. There are, however, many problems not yet solved about the mechanism of hypertension. In particular, although it has been shown that various factors, such as increases in the levels of body fluids, the behavior of the sympathetic nervous system and the existence of hyperinsulinemia, all may have some influence on the development of hypertension in obese individuals, the relative importance of these, and other, factors has been assessed, nor has the mechanism whereby they exert their influence. Recently, it has been shown that obese humans often exhibit increased insulin resistance, as well as hyperinsulinemia and glucose tolerance insufficiency. There have been several reports indicating that hyperinsulinemia and glucose tolerance insufficiency due to obesity may be important factors in the development of obesity-associated hypertension [see, for example, DeFronzo et al.: J. Clin. Invest., 62, 204–213 (1978); Modan et al.: J. Clin. Invest., 75, 809–817 (1985); Reaven & Hoffman: Lancet, 2, 435–436 (1987) Ferrannini et al.: N. Engl. J. Med., 317, 350–357 (1987)].

Accordingly, attempts have been made to cure or alleviate the condition of obese hypertensive patients by improving insulin resistance, and to find an effective therapeutic agent to achieve this.

BRIEF SUMMARY OF INVENTION

We have now discovered a series of thiazolidine derivatives which may be used for the treatment or prophylaxis of obesity-related hypertension. These thiazolidine derivatives can not only reduce insulin resistance but also improve glucose tolerance insufficiency and, unexpectedly, they also exhibit anti-hypertensive activity.

Thus, the present invention provides a method for the treatment or prophylaxis of obesity-related hypertension in a mammal, which may be human, which method comprises administering to said mammal an effective amount of an anti-hypertensive agent selected from the group consisting of thiazolidine derivatives having the formula (I):

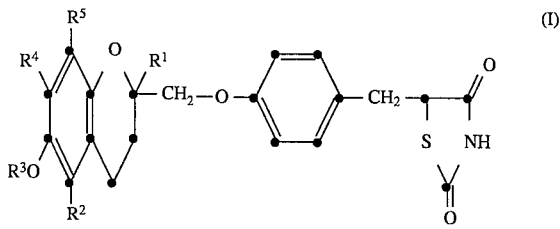

in which:

$R^1$, $R^2$, $R^4$ and $R^5$ are independently selected from the group consisting of hydrogen atoms and alkyl groups having from 1 to 6 carbon atoms; and $R^3$ represents a hydrogen atom, an aliphatic acyl group having from 1 to 7 carbon atoms, an alkoxycarbonyl group having from 2 to 7 carbon atoms, or an arylcarbonyl group in which the aryl part has from 6 to 14 ring carbon atoms and is unsubstituted or is substituted by at least one substituent selected from the group consisting of nitro groups, amino groups, alkylamino groups in which the alkyl part has from 1 to 4 carbon atoms, dialkylamino groups in which each alkyl part has from 1 to 4 carbon atoms, alkoxy groups having from 1 to 4 carbon atom, alkyl groups having from 1 to 4 carbon atoms, hydroxy groups and halogen atoms;

and pharmaceutically acceptable salts thereof.

DETAILED DESCRIPTION OF INVENTION

The compounds of formula (I) used in the present invention are known compounds and are described, for example, in Japanese Patent Application Kokai No. Sho-60-51189, U.S. Pat. No. 4,572,912 and European Patent No. 139 421, the disclosures of which are incorporated herein by reference; they may be prepared as disclosed in those prior Patents. The activity of certain of these compounds is discussed by FuJiwara et al., Diabetes Vol. 37 (1988), pages 1549–1558, and Yoshioka et al., J. Med. Chem., 32 (1989 ), pages 421–428. The compound referred to as CS-045 in those articles is a compound which may be used in the present invention.

In the compounds of formula (I), when $R^1$ represents an alkyl group, this may be a straight or branched chain alkyl group having from 1 to 6, preferably from 1 to 5, carbon atoms, and examples include the methyl, ethyl, propyl, isopropyl, butyl, isobutyl and pentyl groups. Of these, we prefer those alkyl groups having from 1 to 4 carbon atoms, most preferably the methyl group.

When $R^2$ or $R^5$ represents an alkyl group, these may be the same or different and each may be a straight or branched chain alkyl group having from 1 to 6, preferably from 1 to 5, carbon atoms, and examples include the methyl, ethyl, propyl, isopropyl, butyl, isobutyl and pentyl groups. Of these, we prefer those alkyl groups having from 1 to 3 carbon atoms, most preferably the methyl group.

When $R^3$ represents an aliphatic acyl group, this may be a straight or branched chain acyl group having from 1 to 7 carbon atoms and is preferably an alkanoyl group having from 1 to 7 carbon atoms, such as a formyl, acetyl, propionyl, butyryl, isobutyryl, pentanoyl, hexanoyl or heptanoyl group. Of these, we prefer those acyl groups, especially alkanoyl groups, having from 1 to 4 carbon atoms, most preferably the acetyl group.

When $R^3$ represents an aromatic acyl group, this is an arylcarbonyl group in which the aryl part has from 6 to 14, preferably from 6 to 10, and most preferably 6 or 10, carbon atoms, and is substituted or unsubstituted. Thus, the acyl group itself has from 7 to 15, preferably from 7 to 11, and most preferably 7 or 11, carbon atoms. Where the group is substituted, the number of substituents is, in principle, limited only by the number of substitutable positions, e.g. 5 for a phenyl group or 7 for a naphthyl group, however, from 1 to 5 substituents, and more preferably from 1 to 3 substituents, are preferred. Examples of such substituents include:

nitro, amino and hydroxy groups;

alkylamino groups in which the alkyl part has from 1 to 4 carbon atoms, such as the methylamino, ethylamino, propylamino, isopropylamino, butylamino and isobutylamino groups;

dialkylamino groups in which each alkyl part has from 1 to 4 carbon atoms and the two alkyl parts may be the same or different, such as the dimethylamino, diethylamino, dipropylamino, diisopropylamino, dibutylamino, diisobutylamino, methylethylamino, methylpropylamino, methylbutylamino, ethylpropylamino and ethylbutylamino groups;

alkoxy groups having from 1 to 4 carbon atoms, such as the methoxy, ethoxy, propoxy, isopropoxy, butoxy and isobutoxy groups;

halogen atoms, such as the fluorine, chlorine, bromine and iodine atoms, preferably the fluorine or chlorine atoms; and alkyl groups having from 1 to 4 carbon atoms, such as the methyl, ethyl, propyl, isopropyl, butyl and isobutyl groups.

Examples of such substituted and unsubstituted groups include the benzoyl, 4-nitrobenzoyl, 3-fluorobenzoyl, 2-chlorobenzoyl, 3,4-dichlorobenzoyl, 4-aminobenzoyl, 3-dimethylaminobenzoyl, 2-methoxybenzoyl, 3,5-di-t-butyl-4-hydroxybenzoyl and 1-naphthoyl groups. Of these, we prefer the unsubstituted aromatic acyl groups having from 7 to 11 carbon atoms, most preferably the benzoyl group.

When $R^3$ represents an alkoxycarbonyl group, this may be a straight or branched chain alkoxycarbonyl group having from 2 to 7 carbon atoms, i.e. the alkoxy part has from 1 to 6 carbon atoms, and examples include the methoxycarbonyl, ethoxycarbonyl, propoxycarbonyl, isopropoxycarbonyl, butoxycarbonyl, isobutoxycarbonyl, sec -butoxycarbonyl, t-butoxycarbonyl, pentyloxycarbonyl and hexyloxycarbonyl groups. Of these, we prefer those alkoxycarbonyl group having from 2 to 4 carbon atoms, of which the ethoxycarbonyl group is most preferred.

When $R^4$ represents an alkyl group, this may be a straight or branched chain alkyl group having from 1 to 6, preferably from 1 to 5, carbon atoms, and examples include the methyl, ethyl, propyl, isopropyl, butyl, isobutyl, t-butyl and pentyl groups. Of these, we prefer those alkyl groups having from 1 to 4 carbon atoms, more preferably the methyl or t-butyl group, and most preferably the methyl group.

The compounds of the present invention can form salts. There is no particular restriction on the nature of these salts, provided that, where, as in the present invention, they are intended for therapeutic use, they are pharmaceutically acceptable. Where they are intended for non-therapeutic uses, e.g. as intermediates in the preparation of other, and possibly more active, compounds, even this restriction does not apply. The compounds of the present invention contain an acidic group in the thiazolidinedione moiety, and can, therefore, form salts with bases. Examples of such salts include: salts with an alkali metal, such as sodium, potassium or lithium; salts with an alkaline earth metal, such as barium or calcium; salts with another metal, such as magnesium; organic base salts, such as salts with dicyclohexylamine; and salts with a basic amino acid, such as lysine or arginine. Also, where the compound of the present invention contains a basic group in its molecule, it can form acid addition salts. Examples of such acid addition salts include salts with mineral acids, especially hydrohalic acids (such as hydrofluoric acid, hydrobromic acid, hydroiodic acid or hydrochloric acid), nitric acid, carbonic acid, surfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid or citric acid; and salts with amino acids, such as glutamic acid or aspartic acid.

The compounds of the present invention contain asymmetric carbon atoms at the 2-position of the chroman ring and at the 5-position of the thiazolidine ring and can, therefore, form stereoisomers. Although these are all represented herein by a single molecular formula, the present invention includes the use of both the individual, isolated isomers and mixtures, including racemates, thereof. Where stereospecific synthesis techniques are employed or optically active compounds are employed as starting materials in the preparation of the compounds, individual isomers may be prepared directly; on the other hand, if a mixture of isomers is prepared, the individual isomers may be obtained by conventional resolution techniques, or the mixture may be used as it is, without resolution.

A preferred class of compounds of the present invention are those compounds of formula (I) and salts thereof in which:

$R^1$ represents an alkyl group having from 1 to 4 carbon atoms;

$R^2$ represents a hydrogen atom or an alkyl group having from 1 to 3 carbon atoms;

$R^3$ represents a hydrogen atom, an aliphatic acyl group having from 1 to 4 carbon atoms, an unsubstituted aromatic acyl group having 7 or 11 carbon atoms, or an alkoxycarbonyl group having from 2 to 4 carbon atoms;

$R^4$ represents an alkyl group 1 having from 1 to 4 carbon atoms; and $R^5$ represents a hydrogen atom or an alkyl group having from 1 to 3 carbon atoms.

A more preferred class of compounds of the present invention are those compound of formula (I) and salts thereof in which:

$R^1$ represents an alkyl group having from 1 to 4 carbon atoms;

$R^2$ represents a hydrogen atom or an alkyl group having from 1 to 3 carbon atoms;

$R^3$ represents a hydrogen atom or an acetyl, benzoyl or ethoxycarbonyl group;

$R^4$ represents an alkyl group having from 1 to 4 carbon atoms; and $R^5$ represents a hydrogen atom or an alkyl group having from 1 to 3 carbon atoms.

The most preferred class of compounds of the present invention are those compounds of formula (I) and salts thereof in which:

$R^1$ represents a methyl group;

$R^2$ represents a hydrogen atom or a methyl group;

$R^3$ represents a hydrogen atom or an acetyl or ethoxycarbonyl group;

$R^4$ represents a methyl or t-butyl group; and $R^5$ represents a hydrogen atom or a methyl group.

Specific examples of the thiazolidine derivatives of the present invention are those compounds of formula (I), in which $R^1$, $R^2$, $R^3$, $R^4$ and Rare as defined in Table 1 below. In the Table, the following abbreviations are used:

| Ac | acetyl |
|---|---|
| iBu | isobutyl |
| tBu | t-butyl |
| Byr | butyryl |
| Boz | benzoyl |
| Et | ethyl |
| Etc | ethoxycarbonyl |
| Me | methyl |
| Pn | pentyl |

TABLE 1

| Compound No. | $R^1$ | $R^2$ | $R^3$ | $R^4$ | $R^5$ |
|---|---|---|---|---|---|
| 1 | Me | Me | H | Me | Me |
| 2 | H | Me | H | Me | Me |
| 3 | Me | H | H | H | H |
| 4 | Me | H | H | tBu | H |
| 5 | Et | Me | H | Me | Me |
| 6 | iBu | Me | H | Me | Me |
| 7 | Pn | Me | H | Me | Me |
| 8 | Me | Me | Ac | Me | Me |
| 9 | Me | Me | Boz | Me | Me |
| 10 | Me | Me | Etc | Me | Me |
| 11 | Me | H | Ac | Me | H |
| 12 | Me | H | H | Me | H |
| 13 | Me | Me | Byr | Me | Me |

Of the compounds listed above, the preferred individual compounds are Compounds No. 1, 4, 5, 6, 8 and 10; the more preferred compounds are Compounds No.:

1. 5-[4-(6-Hydroxy-2,5,7,8-tetramethylchroman-2-yl-methoxy) benzyl]thiazolidine-2,4-dione;

4. 5-[4-(7-t-Butyl-6-hydroxy-2-methylchroman-2-yl-methoxy)benzyl ]thiazolidine-2,4-dione; and 10. 5-[4-(6-Ethoxycarbonyloxy-2,5,7,8-tetramethyl-chroman-2-ylmethoxy)benzyl]thiazolidine-2,4-dione, as well as pharmaceutically acceptable salts thereof.

Of these, the most preferred compound is Compound No. 1 and pharmaceutically acceptable salts thereof.

The compounds of the present invention can be administered in various forms, depending on the disorder to be treated and the condition of the patient, as is well known in the art. For example, where the compounds are to be administered orally, they may be formulated as tablets, capsules, granules, powders or syrups; or for parenteral administration, they may be formulated as injections (intravenous, intramuscular or subcutaneous), drop infusion preparations or suppositories. These formulations can be prepared by conventional means, and, if desired, the active ingredient may be mixed with any conventional additive, such as a vehicle, a binder, a disintegrator, a lubricant, a corrigent, a solubilizer, an emulsifier or a coating agent. Although the dosage will vary depending on the symptoms, age and body weight of the patient, the nature and severity of the disorder to be treated or prevented, the route of administration and the form of the drug, a daily dosage of from 50 to 5000 mg of the compound may usually be administered to an adult human patient, and this may be administered in a single dose or in divided a doses.

The invention is further illustrated by the following Examples, which illustrate the biological activity of the compounds of the present invention, and the subsequent Preparation, which illustrates the preparation of pharmaceutical formulations suitable for use in the treatment or prophylaxis of hypertension. In these Examples, the compounds of the invention were used in the form of mixtures of stereoisomers prepared as described in U.S. Pat. No. 4,572, 912, without separation. The compounds of the invention are identified by the numbers assigned to them in the foregoing list.

EXAMPLE 1

Anti-hypertensive effect on hypertension with obesity

The anti-hypertensive effect of the compounds of the present invention on obesity-related hypertension was determined using the conventional method.

The test animals used were male Zucker fatty rats, aged 5 or 12 months. They were used in groups of 8. The blood pressure of each rat was determined. The rats were ranked in descending order of their blood pressure, and were put into two groups alternately, one being the control group and the other being the drug administration group. During the period of 3 weeks after the first administration of Compound No. 1 to the drug administration group, the blood pressure of each of the rats was measured once a week by the following non-invasive procedure: The rat was warmed for 5 minutes in a box which had previously been heated at 40° C.; they were then introduced into an acrylic box where they were immobilized. Using apparatus for the non-invasive measurement of blood pressure. [PE-300; a product of Naruko Co. (Japan)], the change in the capacity of the tail region was measured, and the systolic blood pressure was thereby obtained.

The heart rate was calculated as 15 times the pulse rate measured over a period of 4 seconds. The results are shown in Table 2.

TABLE 2

| | Anti-hypertensive effect | |
|---|---|---|
| Blood pressure | Control (mmHg) | Compound No.1 (mmHg) |
| Before administration | 141 ± 7 | 139 ± 7 |
| | (322 ± 28) | (337 ± 16) |
| After 1 week | 147 ± 7 | 131 ± 6 |
| | (334 ± 22) | (344 ± 23) |
| After 2 weeks | 144 ± 7 | 122 ± 2* |
| | (311 ± 34) | (319 ± 19) |
| After 3 weeks | 150 ± 3 | 125 ± 3** |
| | (326 ± 31) | (330 ± 0) |
| 1 week after withdrawal | 150 ± 4 | 145 ± 6 |
| | (349 ± 36) | (335 ± 18) |

Notes:
*$P < 0.05$
**$P < 0.001$

The values in parentheses are heart rates.

As is demonstrated in Table 2, Compound No. 1 was found to exhibit an excellent anti-hypertensive effect on obesity-related hypertension and did not result in any change in heart rate in our animal experiments.

EXAMPLE 2

Acute toxicity

The acute toxicity was studied by conventional means. 300 mg/kg of Compound No. 1 were orally administered to each of 3 male mice of the ddY strain, and the animals were observed for 5 days, during which period all of the mice survived.

In a similar way, Compounds No. 2, No. 3, No. 4 and No. 10 were administered orally. The acute toxicity values of these compounds were all found to be higher than 300 mg/kg.

PREPARATION

Capsules

Powders of the following ingredients were mixed:

| | |
|---|---|
| Compound No. 1 | 100.0 mg |
| Lactose | 168.3 mg |
| Corn starch | 70.0 mg |
| Magnesium stearate | 1.7 mg |
| Total | 340 mg |

The resulting mixture was passed through a 20 mesh sieve (Tyler standard), and 340 mg of the mixture was put into a No. 2 capsule.

As can be seen from the above tests, the compounds of the present invention exhibit an excellent anti-hypertensive effect on obesity-related hypertension without causing any change in heart rate; moreover, they have a low toxicity. Accordingly, they are useful for the prevention and treatment of hypertension accompanied by obesity.

We claim:

1. A method for the treatment of obesity-related hypertension in a mammal, which comprises administration to said mammal an effective amount of an antihypertensive agent wherein said anti-hypertensive agent is selected from the group consisting of 5-[4-(6-hydroxy-2,5,7,8-tetramethylchroman-2-yl-methoxy)benzyl]thiazolidine-2,4-dione and pharmaceutically acceptable salts thereof.

2. The method of claim 1 wherein said antihypertensive agent is 5-[4-(6-hydroxy-2,5,7,8-tetramethylchroman-2-yl-methoxy) benzyl]thiazolidine-2,4-dione.

* * * * *